(12) United States Patent
Jacobson et al.

(10) Patent No.: US 6,428,972 B2
(45) Date of Patent: Aug. 6, 2002

(54) BIOCHEMICAL METHOD TO MEASURE NIACIN STATUS IN A BIOLOGICAL SAMPLE

(75) Inventors: Elaine L. Jacobson; Myron K. Jacobson, both of Lexington, KY (US)

(73) Assignee: Niadyne, Inc., Tucson, AZ (US)

( * ) Notice: Subject to any disclaimer, the term of this patent is extended or adjusted under 35 U.S.C. 154(b) by 0 days.

(21) Appl. No.: 09/871,259

(22) Filed: May 31, 2001

Related U.S. Application Data

(62) Division of application No. 09/334,782, filed on Jun. 16, 1999, now Pat. No. 6,287,796.
(60) Provisional application No. 60/089,615, filed on Jun. 16, 1998.

(51) Int. Cl.[7] .................................. C12Q 1/32
(52) U.S. Cl. ......................... 435/26; 435/188
(58) Field of Search .................... 435/26, 188

(56) References Cited

U.S. PATENT DOCUMENTS

| | | | |
|---|---|---|---|
| 3,616,258 A | 10/1971 | Kronish et al. | 195/103.5 |
| 5,879,880 A | 3/1999 | Koca et al. | 435/4 |
| 6,020,351 A | 2/2000 | Pero | 514/355 |
| 6,287,796 B1 * | 9/2001 | Jacobson et al. | 435/26 |

OTHER PUBLICATIONS

Jacobson, et al., "Mapping The Role of NAD metabolism in prevention and treatment of carcinogenesis," Mol & Cell. Biochem 193:69–74 (1999).

Shieh, et al., "Poly (ADP–ribose) Polymerase Null Mouse Cells Synthesize ADP–ribose Polymers." J. Biol. Chem 273(46): 30069–30072 (1998).

Jacobson, et al., "Tissue NAD as a Biochemical Measure of Niacin Status In Humans," Meth. Enzymol 280: 221–230 (1997).

Jacobson, et al., "Evaluating the role of niacin in human carcinogenesis," Biochimie 77:394–398 (1995).

Harper, et al., "Niacin Status Assessment in Evaluation of Cancer" FASEB J 8(4–5)A719 (1994).

Jacobson, et al., "A biomarker for the assessment of niacin nutriture as a potential preventive factor in carcinogenesis," J. Intern. Med. 233:59–62 (1993).

Jacobson, "Niacin Deficiency and Cancer In Women," J. Am. Coll. of Nut. 12(4): 412–416 (1993).

Robins, et al., "Effect of Hyperthermia In Vitro and In Vivo on Adenine and Pyridine Nucleotide Pools in Human Peripheral Lymphocytes," Cancer 67(8): 2096–2102 (1991).

Fu, et al., "Biochemical Markets For Assessment of Niacin Status in Young Men. Levels of Erythrocyte Niacin Coenzymes and Plasma Tryptophan," T. Nutrition 119(12):1949–1955 (1989).

Jonsson, et al., "Mechanism of Alteration of Poly(Adenosine Diphosphate–Ribose) Metabolism by Hyperthermia," Canc. Res. 48:4233–4239 (1988).

Shibata, et al., "Blood NAD as an index of Niacin Nutrition." Nut. International 2(3):117–181 (1986).

Jacobson, et al., "Effect of Nicotinamide Analogues on Recovery from DNA Damage In C3H10T½ Cells," Canc. Res. 44:2485–2492 (1984).

Jacobson, et al., "Poly (ADP–ribose) Metabolism In Ultraviolet Irradiated Human Fibroblasts," J. Biol. Chem. 258(1): 103–107 (1983).

* cited by examiner

*Primary Examiner*—Ralph Gitomer
(74) *Attorney, Agent, or Firm*—Fulbright & Jaworski LLP.

(57) ABSTRACT

The invention relates to assay or determining intercellular niacin status in solid tissues. One extracts intracellular pyredine nucleotides, cycles these, in the presence of agents which reduce the pyredine nucleotides and a dye, which reflect the change. Changes in absorbance of the dye molecule permit determination of the niacin status.

17 Claims, 1 Drawing Sheet

NAD Cycling Assay

BIOCHEMICAL METHOD TO MEASURE NIACIN STATUS IN A BIOLOGICAL SAMPLE

CROSS REFERENCE TO RELATED APPLICATION

This application is a divisional of application Ser. No. 09/334,782, filed Jun. 16, 1999 now U.S. Pat. No. 6,287,796, which claims the benefits of U.S. Provisional Application Serial No. 60/089,615, filed Jun. 16, 1998. The entire disclosure of U.S. Provisional Application 60/089,615 is incorporated by reference.

STATEMENT REGARDING FEDERALLY SPONSORED RESEARCH OR DEVELOPMENT

The present invention was supported in part by the National Institutes of Health (Grant CA43894 and CA65579). The Government may have certain rights in the invention.

TECHNICAL FIELD

The present invention relates to a biochemical methods, and kits to measure the niacin status of an individual, particularly to a colorimetric method for the detection of intracellular pyridine nucleotide content or concentration in a biological sample such as whole blood or tissues.

BACKGROUND OF THE INVENTION

Niacin, also called nicotinic acid, pyridine 3-carboxylic acid, vitamin B3 or vitamin PP, is a water soluble vitamin. The known biological roles of niacin are attributable to the function of its active metabolites, nicotinamide adenine dinucleotide (NAD) and nicotinamide adenine dinucleotide phosphate (NADP).[1] As used herein, pyridine coenzymes or pyridine nucleotides refer to NAD and NADP. NAD and NADP represent the total oxidized and reduced pools of each nucleotide, respectively. Thus, NAD represents the sum of $NAD^+$ and NADH while NADP represents the sum of $NADP^+$ and NADPH.

[1] NAD is also called diphosphopyridine nucleotide (DNP) and conenzyme I or cozymase. NADP is also called triphosphopyridine nucleotide (TPN) or coenzyme II. These alternative names are not popular or are no longer used.

In humans, niacin equivalents can be obtained from dietary nicotinate, nicotinamide, and tryptophan. Consequently, niacin status depends on the amount of these in the diet and on factors that influence uptake, distribution, efficiency of conversion to tissue NAD and NADP, and excretion or reutilization of the nicotinamide moiety formed by the turnover of NAD and NADP. The term niacin number has been chosen as a convenient way to represent niacin status and is defined as the ratio of the concentration of NAD to the concentration of NADP multiplied by 100 (100·[NAD]/[NADP]) in whole blood. For example, if the relative concentration of NADP([NADP]) is 1 and the relative concentration of NAD([NAD]) is 0.72, the niacin number would be 72 (from the formula 100·[NAD]/[NADP]=72 wherein [NAD] is 0.72 and [NADP] is 1). Expressing the values in this way yields a whole number that is linearly related to intracellular NAD content of red blood cells.

Attempts have been made to measure niacin status in a subject. Previous attempts have involved the determination of urinary metabolites of nicotinamide (R. A. Jacob et al., *J. Nutr.* 119, 591 (1989)). In these tests the urinary excretion of niacin or niacin metabolites are measured to infer the niacin status in a subject. These attempts involve multiple biochemical steps that are labor intensive, and slow and do not measure niacin bioavailability or intracellular niacin active metabolites directly. Thus, current methods for measuring niacin status are not suitable to wide-scale screening and the relationship of the nicotinamide metabolites to niacin status is still poorly understood.

A metabolic ward study has shown that the NAD content of erythrocytes is a sensitive marker for niacin status in humans (C. S. Fu et al., *J. Nutr.* 119, 1949 (1989)). Test subjects restricted to a niacin intake of approximately 50% of the recommended daily allowance showed a 70% decrease in NAD content after five weeks. In contrast, NADP content remains relatively constant throughout the niacin restricted diet period (C. S. Fu et al., *J. Nutr.* 119, 1949 (1989)). Thus, because the NADP concentration remains constant while the NAD concentration is affected by niacin intake, the ratio of NAD to NADP reflects niacin status. Niacin status refers to the bioavailability of niacin and niacin derivatives such as NAD and NADP inside a cell and is an indication of the bioavailability of NAD. Because more than 98% of the total pyridine nucleotide pool of whole blood is in the erythrocyte fraction, (E. L. Jacobson and M. K. Jacobson, *J. Int. Med.* 233, 59 (1993)) niacin status can be obtained from a few microliters of whole blood. One aspect of the invention is directed to a method of assessment of niacin status which is inexpensive, relatively accurate and rapid, and suitable to wide scale-application in the human population.

Niacin status derived from erythrocytes or whole blood from humans varies over a wide range. The data of Table I show the mean niacin number and the range of values measured in several populations. Using data from a nonrandom population of free living healthy adults and metabolic ward subjects on controlled niacin intake (C. S. Fu et al., *J. Nutr.* 119, 1949 (1989)), the mean niacin number is found to be approximately 175 and from the standard deviation it is predicted that 95% of the population would have values between 127 and 223. In a separate study of a large population of 46- to 64-year-old individuals in Malmö, Sweden a range of 28 to 337 was seen, with a mean of 160. The effect of dietary niacin intake on niacin status was shown in a study of individuals undergoing niacin therapy where the average pretherapy value of 175 was increased to 665 by niacin supplements. Taken together these data illustrate that niacin status varies widely in the human population and can be modulated by niacin supplementation.

TABLE I

NIACIN STATUS IN HUMAN POPULATIONS

| Population studied | n | Mean niacin number | Range observed |
|---|---|---|---|
| Metabolic ward controls[a] (100% of RDA for niacin) | 7 | 178 ± 36 | N/A[b] |
| Metabolic ward subjects[a] (50% RDA, 5 weeks) | 7 | 62 ± 11 | N/A |
| Healthy adults (United States)[c] | 30 | 175 ± 24 | 132–211 |
| Healthy adults, 46–64 years old (Malmö, Sweden)[d] | 687 | 160 ± 37 | 28–337 |
| Hypercholesterolemia subjects[e] Pretherapy | 5 | 175 ± 45 | 131–242 |
| Two months of niacin therapy | 10 | 665 ± 115 | 517–746 |

[a]Calculated from the data in Ref. 3. RDA, U.S. recommended dietary allowance
[b]N/A, Not available.
[c]A nonrandom population of health-conscious adults, most of whom supplement their diet with a multiple vitamin containing the U.S. recommended dietary allowance for niacin.

TABLE I-continued

NIACIN STATUS IN HUMAN POPULATIONS

| Population studied | n | Mean niacin number | Range observed |
|---|---|---|---|

[d]Blood samples were provided by the Malmö Diet and Cancer Study via a grant from the Texas Higher Education Coordinating Board Advanced Research Grant 009768-025.
[e]Blood samples from hypercholesterolemia subjects were provided by H. I. Robins, University of Wisconsin Clinical Cancer Center and the University of Wisconsin Lipid Clinic. Subjects received 750 mg of niacin twice daily for two months.

The assay of the invention is useful for determining the optimal amounts of dietary niacin to obtain an optimal level of intracellular niacin metabolites (niacin number). NAD is involved with ADP-ribose transfer reactions and these reactions have been implicated in a number of metabolic signaling processes (M. K. Jacobson, et al., in ADP-Ribosylating Toxins and G Proteins: Insights into Signal Transduction, J. Moss and M. Vaughan, eds., p. 479 American Society for Microbiology, Washington, DC 1990; K. C. Williamson and J. Moss, in ADP-Ribosylating Toxins and G Proteins: Insights into Signal Transduction, J. Moss and M. Vaughan, eds., p. 493. American Society for Microbiology, Washington, D.C., 1990; M. A. De Matteis et al., *Proc. Natl. Acad. Sci. U.S.A.* 91, 1114 (1994); H. C. Lee et al., *Vitam. Horm.* 48, 199 (1994); F.-J. Zhang et al., *Bioorg. Med. Chem. Lett.* 5,2267 (1995); C. Q. Vu et al., *J. Biol. Chem.* 271, 4747 (1996)) and in cellular recovery from DNA damage (F. R. Althaus and C. Richter, "ADP-Ribosylation of Proteins: Enzymology and Biological Significance." Springer-Verlag, Berlin, 1987). For example, studies of the conversion of NAD to ADP-ribose polymers in response to DNA damage indicate that an optimal cellular content of NAD may be a preventive factor in cancer (E. L. Jacobson and M. K. Jacobson, *J. Int. Med.* 233, 59 (1993); E. L. Jacobson et al., in ADP-Ribosylating Reactions, G. G. Poirier and P. Moreau, eds., p. 153. Springer-Verlag, New York, 1992). Such studies have shown a need for a rapid and accurate method for measuring niacin content based on tissue NAD in humans.

There is a need for a highly sensitive, accurate and reliable method to determine niacin status as measured by intracellular NAD content relative to the intracellular NADP content in a subject in order to conveniently and rapidly assay the niacin state in a subject. Such a method should be inexpensive, easy to manufacture as a kit, easy to use, adaptable to current laboratory equipment, and be capable of miniaturization and automation.

BRIEF SUMMARY OF THE INVENTION

The present invention is directed to meeting the foregoing needs by providing a simple and convenient method of assaying intracellular pyridine nucleotide in a subject. The subject may be a mammal, such as, for example, a human being. The invention can be applied to the field of medicine where measurement of niacin is undertaken in diagnosis involving human subjects.

One advantage of the method of the invention is that it has high sensitivity and a wide range of linearity, thus enabling the direct and rapid measurement of pyridine nucleotides in biological fluids containing cells such as blood without sample concentration or dilution.

Interest in measuring niacin and pyridine nucleotide in humans has increased since it was demonstrated that total pyridine nucleotide concentrations reflect niacin intake in humans and that niacin plays a role in prevention of cancer. Prior art methods of niacin measurement require expensive, laborious analyses of oxidized products of niacin in urine or even more tedious assays of nicotinamide and/or nicotinic acid in serum. The current methods are disadvantageous at least because they do not measure the intracellular active forms of niacin, NAD and NADP. Thus, a need has arisen for a simple and effective way to measure niacin status.

This need has been met by the present invention. The present invention involves a novel double extraction procedure that can allow quantification of total pyridine nucleotides from blood cells from samples as small as 10 $\mu$L of whole blood. The present invention avoids the above noted disadvantages of prior art niacin measurement methods and provides unique advantages over all prior approaches to assessing niacin status in humans. One advantage of the method is that it is capable of directly measuring intracellular NAD and NADP. Because the measurement is extremely sensitive, it can be made using a very small amount of blood. The 10 $\mu$L of blood required for the assay is typically available as a residual amount of blood drawn for other clinical measurements.

Another advantage of the method is that pyridine nucleotides are assayed directly by the addition of a few solutions with no additional fractionation, concentration, or dilution steps. Further, it has been demonstrated that the extraction procedure results in the complete extraction of total pyridine nucleotides (NAD and NADP) without any losses of either the oxidized or reduced forms of the nucleotides. Another advantage of the method is that the amount of manual labor to perform each assay is minimal and thus highly adaptable to automated or semiautomated operation. For example, a skilled operator using a multichannel pipette (Sigma, St. Louis) with (8, 12 or 96 channels) may perform assays using one (96 assays), two (192 assays), three (288 assays) or four (384 assays) or more microtiter dishes simultaneously. For example, the centrifugation steps of the method may be performed directly on a microtiter dish using a microtiter dish centrifuges (Beckman, Fullerton, Calif.).

The methods of the invention may be used in the context of health maintenance and disease prevention. Given the role of niacin in the biological responses of a cell to carcinogenic insults, the niacin status of an individual may be a critical factor in determining the overall ability of an individual to withstand such insults. The simplicity of the method and the small amount of sample required make it particularly well suited for adaption to a home test kit for niacin status. In an embodiment, a home test kit may comprise a lancet and a tube for blood. The user simply need to draw about 10 $\mu$L to 100 $\mu$L of blood, mix the blood with anticoagulant, and send the sample to the laboratory for analysis. The anticoagulation step may be performed by adding a small amount of anticoagulant to the collected blood. Alternatively, to simplify the collection process, the anticoagulants may be incorporated into the collection tube, such as, for example, as a dry coating in a collection kit for the consumer.

The invention is now described in the following specific embodiments:

Assaying Intracellular Pyridine Nucleotide

One embodiment of the invention is directed to a method of assaying an intracellular pyridine nucleotide status of a biological sample. The method comprises obtaining the biological sample and extracting the intracellular pyridine nucleotide from the biological sample. The amount of pyridine nucleotide in the sample is detected in a cycling process which is summarized in FIG. 1. Briefly, the cycling process contains the following two steps which can be performed in any order. In the first step, the pyridine nucleotide is reduced to a reduced pyridine nucleotide. In the second step, an electron from the reduced pyridine nucleotide is transferred to an electron acceptor dye molecule. The transfer of an electron from the reduced pyridine nucleotide to the electron acceptor dye compound causes the reduced pyridine nucleotide to become oxidized. Thus, after this second step, the first step may be performed to reduce the pyridine nucleotide again.

It is understood that in some instances, the extracted pyridine nucleotide is already reduced and thus the reaction is started by step 2 first (transfer electron to dye) followed by step 1 (reduce pyridine nucleotide). It is further understood that both steps may be performed in any particular order and preferably the two steps are performed simultaneously. That is the reduction of pyridine nucleotide may be performed in the same reaction where an electron from the reduced nucleotide is transferred to the electron acceptor dye. For example, an enzyme and enzyme substrate pair (discussed in a later section) may be added to reduce pyridine nucleotide at the same time a electron acceptor dye and an electron transmitter compound (discussed in a later section) is added to remove electron from the pyridine nucleotide.

The result of the cyclic reaction is that an electron is transferred to an electron acceptor dye (the dye is reduced) at a rate that is proportional to the amount of pyridine nucleotide present in the sample. The reduction of the electron acceptor dye is measured to determine the amount of pyridine nucleotide in the biological sample. The reduction of the electron acceptor dye may be measured by a shift in absorbance of the dye in response to the accepted electron. The exact amount of pyridine nucleotide present may be determined by first performing the method of the invention with different known amounts of pyridine nucleotide and recording the reduction of the electron acceptor dye in response to each quantity of pyridine nucleotide. A correlation curve may be drawn to show the correlation between the pyridine nucleotide present and the shift in absorbance of the dye (amount of electron acceptor dye reduction). Then the method is used to determine the pyridine nucleotide of an unknown sample. The amount of shift in absorbance is compared to the correlation curve to determine the amount of pyridine nucleotide in the unknown sample.

One advantage of the method is that it is highly sensitive. The cycling reaction allow one pyridine nucleotide to facilitate the transfer of multiple electrons to an electron acceptor dye. In this way the signal is amplified. Further, the reaction proceeds linearly with time such that the reaction time may be lengthened to increase the sensitivity. The pyridine nucleotides (NAD and NADP) is stable for at least 1.5 hours. Thus, the detecting step may be, for example, about one minute, about 3 minutes, about 5 minutes, about 10 minutes, about 15 minutes, about 30 minutes, about 60 minutes, about 90 minutes, about 120 minutes or longer or any value of time in between.

The transfer of an electron to the electron acceptor dye causes a change in the absorbance of the dye. This change may be measured by eye. More preferably, the change in absorbance is measured by a photospectrometer. Depending on the electron acceptor dye used, the change may be in the visible, infra red, or ultraviolet region of the spectrum.

The pyridine nucleotide to be measured may be NAD or NADP. It is understood that NAD refers to the reduced form (NAD$^+$) and the oxidized form (NADH). It is understood that NADP refers to the reduced form (NADP$^-$) and the oxidized form (NADPH).

The Biological Sample

The biological sample may be whole blood or a solid tissue obtained from a subject. The subject may be any animal. Preferably, the animal is a mammal. Even more preferably, the mammal is a human. The biological sample may be any tissue from the subject that comprises whole cells. One advantage of the method of the invention is that an intracellular niacin status may be determine from whole blood. If the assay is performed immediately, whole blood may be used directly. If a period of time, such as a few minutes is to pass between the collection of the sample and the assay, then the whole blood should be anticogulated.

The extraction step comprises disrupting the cells in the biological sample and removing proteins from the disrupted cells. In a preferred embodiment, disruption is performed by treating the biological sample with a basic compound for a period of less than about 2 minutes at less than about 4° C. followed by neutralizing the basic compound. Alternatively, a frozen biological sample may first be disrupted by mechanical means in liquid nitrogen before treatment with a basic compound and neutralization. Protein removal may be performed by an acid precipitation or salt precipitation of proteins. Acid precipitation may involve acid precipitation of proteins followed by neutralization of the acid.

A Cycling Reaction to Quantitate Pyridine Nucleotide

The amount of pyridine nucleotide in the extract is quantitated by a two step cycling reaction. In one step of the cycling reaction, pyridine nucleotide is reduced. Reduction may be performed by adding an enzyme and enzyme substrate pair to the extracted pyridine nucleotide. For the measurement of NAD, the enzyme and enzyme substrate pair may be alcohol dehydrogenase and ethanol; malate dehydrogenase and malate; lactate dehydrogenase and lactate; cytoplasmic isocitrate dehydrogenase (cytoplasmic) and isocitrate; glyceraldehyde-3-phosphate dehydrogenase and glyceraldehyde-3-phosphate; or a combination of these enzyme and enzyme substrate pairs. For the measurement of NADP, the enzyme and enzyme substrate pair may be mitochondrial isocitrate dehydrogenase and isocitrate; glucose-6-phosphate dehydrogenase and glucose-6-phosphate; 6-phosphogluconate dehydrogenase and 6-phosphogluconate; malic enzyme and malate; mitochondrial isocitrate dehydrogenase and isocitrate; or a combination of these enzyme and enzyme substrate pairs. After reduction, the pryidine compounds NAD and NADH should be reduced to NADH only. Similarly, the pryidine compounds NADP and NADPH should be reduced to NADPH only. The method is not limited to any particular enzyme and enzyme substrate pair. Any enzyme and enzyme substrate capable of reducing NAD and NADP may be used. Other NAD specific or NADP specific enzymes may be determined by consulting standard biochemical references. Such pairs may include artificial or genetically engineered enzymes and substrates. In addition, total pyridine nucleotide (NAD and NADP) may be measured together by adding NAD and NADP specific enzyme. Naturally, because the total pyridine nucleotide concentration is equal to the sum of the NAD concentration and NADP concentration, NAD concentration is equal to total pyridine concentration minus NADP concentration. Similarly, NADP concentration is equal to total pyridine concentration minus NAD concentration.

In the second step of the cycling reaction, an electron is transferred from the reduced pyridine nucleotide to an electron acceptor dye. An electron may be transferred from the reduced pyridine nucleotides (NADH or NADPH) to an electron acceptor dye via intermediate electron transmitter compound. Any electron transmitter compound capable of accepting an electron from a reduced pyridine nucleotide and transferring an electron to an electron acceptor dye molecule may be used. Preferred electron transmitter compound include, for example, oxidized phenazine ethosulfate (PES(ox)), 5-methylphenazinium methylsulfate, 1-methoxy-5-methylphenazinium methylsulfate, diaphorase (dihydrolipoamide reductase, EC 1.6.4.3.) or a combination of these electron transfer compounds. In the transfer reaction, the electron from NADH or NADPH is first transferred to an electron transmitter compound, then an electron from electron transfer compound is transferred to an electron acceptor dye molecule.

After the second step of the cycling reaction, the pyridine nucleotide is oxidized again. That is NADH is converted to NAD and NADPH is converted to NADP. The oxidized pyridine nucleotide may serve as substrate for the first step of the cycling reaction—the reduction of pyridine nucleotide. The cycle may be repeated many time to generate a detectable signal from a small concentration of pyridine nicleotide.

The Electron Acceptor Dye

The electron acceptor dye molecule may be any dye molecule that shows a detectable absorbance change after acceptance of an electron. Preferred electron acceptor dye compound include, for example, thiazolyl blue (MTT), 3,3'-(3,3'-dimethoxy-4,4'-biphenylene)-bis(2-(p-nitrophenyl)-2H-tetrazolium chloride) (NBT), 3-(p-indophenyl)-2-(p-nitrophenyl)-5-phenyl-2H-tetrazolium chloride (INT), 3,3'-(4,4'-biphenylene)-bis(2,5-diphenyl-2H-tetrazoliumchloride), 3,3'-(3,3'-dimethoxy-4,4'-biphenylene)-bis(2,5-diphenyl-2H-tetrazolium chloride), 3,3'-(3,3'-bis(2,5-bis(p-nitrophenyl)-2H-tetrazolium chloride) and a combination of these dyes.

Calculation of Niacin Status

Another embodiment of the invention is directed to a method of calculating a niacin status in a biological sample. A niacin status may be express as niacin number=(100·[NAD]/[NADP]) or expressed as a ratio of NAD to total nucleic acid, NAD to total protein, NADP to total nucleic acid or NADP to total protein. To calculate a niacin number, any method of the invention is used to determine the amount of NAD in a biological sample. Any method of the invention is used to determine the amount of NADP in a biological sample. The niacin status, expressed as a niacin number, may be derived from the formula: niacin number=(100·[NAD]/[NADP]).

Alternatively, it is possible to determine the ratio of pyridine nucleotide to total cellular nucleic acid (DNA, RNA or DNA+RNA) or to total cellular protein. The pyridine nucleotide, which may be the amount of NAD or the amount of NADP is measured using any of the methods of the invention. Total cellular DNA or total cellular protein may be measured using standard methods. A ratio of pyridine nucleotide to total cellular DNA or protein can be calculated from the results.

Measuring Niacin Status from Whole Blood

Another embodiment of the invention is directed to a method to measure intracellular niacin status in whole blood. In the method, a whole blood sample is collected. Intracellular pyridine nucleotide is extracted from the whole blood sample. A cycling reaction, as discussed above, is used to transfer an electron to an electron acceptor dye. After the cycling process, the change in absorbance of the electron acceptor dye molecule is measured to determine the intracellular pyridine nucleotide status. The method may be performed immediately after collection of whole blood. Alternatively, if the method cannot be performed immediately, the whole blood may be anticogulated.

Measuring Reduced Intracellular Pyridine Nucleotide

Another embodiment of the invention is directed to a method for measuring a reduced intracellular pyridine nucleotide in a biological sample. In the method, a biological sample is provided. The reduced intracellular pyridine nucleotide from the biological sample is extracted with hot alkaline treatment as described in the Examples section. Briefly, the sample is placed in ice-cold 1.0 M NaOH extract and then heated with stirring at 60° C. for 10 min. The amount of NaOH used may be, for example, about 0.1 volume, about 0.3 volume, about 0.5 volume, about 1 volume, about 3 volume, about 5 volume or about 10 volume of the biological sample. After the hot alkaline treatment, the sample is neutralized, and chilled. The heating destroys oxidized nucleotides and the resulting extract is a measure of the reduced pyridine nucleotides. The reduced intracellular pyridine nucleotide is used to mediated the transfer of an electron to an electron acceptor dye using the cycling reaction as described in the section entitled "A Cycling Reaction to Quantitate Pyridine Nucleotide." The change in absorbance of the electron acceptor dye molecule is measured to determine the amount of intracellular reduced pyridine nucleotide.

Measuring Total Intracellular Pyridine Nucleotide

Another embodiment of the invention is directed to a method for measuring a total intracellular pyridine nucleotide in a biological sample. In the method, a biological sample is provided. The reduced intracellular pyridine nucleotide from the biological sample is extracted with cold acid treatment as described in the Examples section. Briefly, the sample is placed in ice-cold 1.0 M NaOH extract. The sample is neutralized immediately with ice-cold $H_3PO_4$. Neutralization refers to the addition of acid, base or a buffer to a solution until the pH is between about 5 and about 10, preferably between about 6 and about 8, more preferably between about 6.5 to 7.5 and most preferably about 7. The extracted total intracellular pyridine nucleotide is used to mediated the transfer of an electron to an electron acceptor dye using the cycling reaction as described in the section entitled "A Cycling Reaction to Quantitate Pyridine Nucleotide." The change in absorbance of the electron acceptor dye molecule is measured to determine the amount of intracellular total pyridine nucleotide.

Kits

Another embodiment of the invention is directed to a kit for the extraction of intracellular pyridine nucleotides from a biological sample. The kit may comprise a base solution, an acid solution, a neutralizing solution, and an electron acceptor dye. The base solution may be NaOH, the acid solution may be $HClO_4$ and the neutralizing solution may be KOH. The electron acceptor dye may be any dye that can accept an electron from NAD, NADP or an electron transmitter compound. Examples of preferred dyes include thiazolyl blue (MTT); 3,3'-(3,3'-dimethoxy-4,4'-biphenylene)-bis(2-(p-nitrophenyl)-2H-tetrazolium chloride) (NBT); 3-(p-indophenyl)-2-(p-nitrophenyl)-5-phenyl-2H-tetrazolium chloride (INT); 3,3'-(4,4'-biphenylene)-bis(2,5-diphenyl-2H-tetrazoliumchloride); 3,3'-(3,3'-dimethoxy-4,4'-biphenylene)-bis(2,5-diphenyl-2H-tetrazolium chloride); 3,3'-(3,3'-bis(2,5-bis(p-nitrophenyl)-2H-tetrazolium chloride); and a combination thereof When multiple dyes are used in a reaction, the absorbance of each dye may be measured individually.

The kit may optionally comprise one or more of the following: an electron transfer compound, an enzyme and enzyme substrate pair, NAD or NADP pyridine nucleotide standard, and instructions for performing an intracellular pyridine nicleotide assay using any of the methods of the invention.

The electron transfer compound of the kit may be any compound capable of accepting an electron from a reduced pyridine nucleotide and transferring an electron to an electron accentor dye molecule. Examples of electron transmitter compound include oxidized phenazine ethosulfate (PES (ox)); 5-methylphenazinium methylsulfate; 1-methoxy-5-methylphenazinium methylsulfate; diaphorase (dihydrolipoamide reductase, EC 1.6.4.3.); and a combination of these compounds.

The enzyme and enzyme substrate pair of the kit may be any enzyme and enzyme substrate that together can cause a reduction of NAD or NADP. In a kit or a reaction designed to measure NAD, the enzyme and enzyme substrate should be specific for reducing NAD. Similarily, in a kit or a reaction designed to measure NADP, the enzyme and enzyme substrate should be specific for reducing NADP. If both NAD and NADP is measured in one reaction, the enzyme and enzyme substrate need not be specific for reducing NAD or NADP but can reduce both pyridine nucleotides. Examples of preferred enzyme and enzyme substrates include alcohol dehydrogenase; ethanol; malate dehydrogenase; malate; lactate dehydrogenase; lactate; NAD specific isoctirate dehydrogenase; isocitrate; glyceraldehyde-3-phosphate dehydrogenase; glyceraldehyde-3-phosphate; glucose-6-phosphate dehydrogenase; glucose-6-phosphate; 6-phosphogluconate dehydrogenase; 6-phosphogluconate; malic enzyme; malate; NADP specific isocitrate dehydrogenase; and a combination thereof.

DETAILED DESCRIPTION OF THE INVENTION

Figure 1:
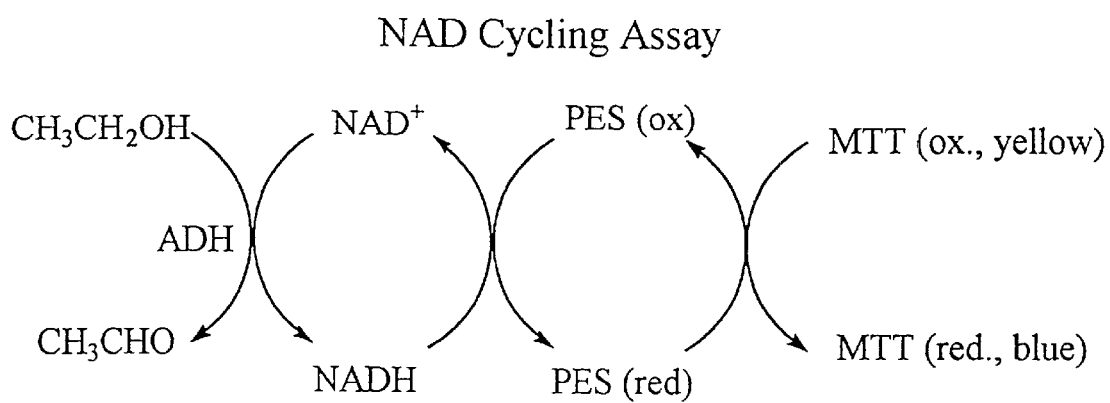
FIG. 1 depicts a schematic representation of the cycling assay used to determine NAD.

As used herein, a compound refers to a chemical molecule or salt thereof that is either in a substantially pure (reagent grade purity) form or in a solution. Examples of compounds include $NAD^-$, $NADP^+$, NADH, NADPH, NaOH, $H_3PO_4$, KOH, EtOH, oxidized phenazine ethosulfate (PES(ox)), thiazolyl blue (MTT), 5-methylphenazinium methylsulfate, 1-methoxy-5-methylphenazinium methylsulfate, diaphorase (dihydrolipoamide reductase, EC 1.6.4.3.), 3,3'-(3,3'-dimethoxy-4,4'-biphenylene)-bis(2-(p-nitrophenyl)-2H-tetrazolium chloride) (NBT), 3-(p-indophenyl)-2-(p-nitrophenyl)-5-phenyl-2H-tetrazolium chloride (INT), 3,3'-(4,4'-biphenylene)-bis(2,5-diphenyl-2H-tetrazoliumchloride), 3,3'-(3,3'-dimethoxy-4,4'-biphenylene)-bis(2,5-diphenyl-2H-tetrazolium chloride), and 3,3'-(3,3'-bis(2,5-bis(p-nitrophenyl)-2H-tetrazolium chloride). These compounds may be supplied as a reagent grade crystal or as a solution. The solutions may be, for example, an aqueous solution.

As used herein, an enzyme/enzyme substrate pair refers to any enzyme and an enzyme substrate for that enzyme such that the action of the enzyme on the enzyme substrate causes either (1) the reduction of NAD+ to NADH or (2) the reduction of NADP+ to NADPH. Natural, genetically engineered, and synthetic enzymes and substrates are contemplated by the invention.

Niacin status is a well known term of art (e.g., described in Nutrition Reviews (1990), vol 48, pg 318; and Sauberlich, Annu Rev Nutr (1984) 4: 377–407) and refers to the niacin and niacin metabolite bioavailability in a subject. Niacin status may be represented as a niacin number. In addition, niacin status may be defined as a ratio between pyridine nucleotides (NAD and NADP) and a constant cellular constituent such as total protein or total nucleic acid. Niacin status may be represented also as a ratio between pyridine nucleotides (NAD or NADP) and cellular DNA; or between pyridine nucleotides and cellular protein.

One embodiment of the invention is directed to a method of assaying a pyridine nucleotide content of a biological sample. Pyridine nucleotide refers to NAD and NADP and the pyridine nucleotide content of a cell maybe used to determine niacin status. NAD content refers to the sum of $NAD^+$ and NADH while NADP content refers to the sum of $NADP^+$ and NADPH. The method may be used to measure NAD content, NADP content or both NAD and NADP content of a biological sample.

Another embodiment of the invention is directed to a method of determining a niacin status such as a niacin number for a biological sample. The niacin number may be derived from the concentration of NAD and NADP according to the formula niacin number=100×(NAD/NADP).

In the method, a biological sample is first obtained from a subject. The pyridine nucleotide is extracted from the biological sample and the pyridine nucleotide to be measured is selectively reduced to a reduced pyridine nucleotide. For example, if NAD is to be measured, NAD is reduced to NADH and if NADP is to be measured, NADP is reduced to NADPH. The reduced pyridine nucleotide, NADH or NADPH, is used to reduce an intermediate electron transfer compound in an reaction that results in the transfer of an electron from the reduced pyridine nucleotide to the electron transfer compound. The transfer of electrons from the intermediate acceptor to a final dye acceptor results in a cycling process that amplifies the signal by ultimate transfer to and accumulation of a final dye acceptor which results in a change in absorbance (optical density) of the electron acceptor dye molecule. If the absorbance change is in the visible spectrum, it may be perceived as a change in color of the dye. The pyridine nucleotide content (NAD content or NADP content) is calculated from the change in optical density of the electron acceptor dye molecule.

The biological sample may be a blood sample. The blood is preferably whole blood containing at least erythrocytes. Another advantage of the invention is that the method may be performed on blood which was collected and stored using general blood collection procedures. Blood collected for transfusion or assays, for example, are often anticogulated. The methods of the invention are usually unaffected by normal anticoagulants such as heparin, EDTA, sodium citrate, and sodium fluoride. Thus, no special procedure, besides procedures for collecting anticogulated blood, is required for the blood collection part of the method of the invention. Another advantage of the method is that the amount of blood required, 100 µL, may be collected using capillary blood sampling techniques such as blood lancets. In such an application, a few drops of blood may be collected and immediately deposited in a tube with an anticoagulant. Capillary blood sampling reduces the risks, training, and cost associated with standard blood collection techniques such as venipuncture.

For long term stability of the collected blood, it may be desirable to add a small quantity of an antimicrobial agent to the blood to prevent growth of microorganisms. An antimicrobial agent may be an antibiotic, a synthetic antibacterial compound or a poison. Antibiotics are naturally found substances that can destroy or inhibit the growth of other microorganisms. Antibiotics may be synthesized synthetically. An antibacterial compound is a synthetic substance that can destroy or inhibit the growth of microorganisms. More than 100 antibiotics and 100 antibacterial compounds are known and listed in the Merck Index (therapeutic category, antibiotic and antibacterial entries, 11$^{th}$ edition, Merck & Co. Rahway, N.J., 1989) which is incorporated herein by reference.

Another advantage of the assay is that it allows for measurement of pyridine nucleotides from any tissue in a subject that contains intact cells such as dermal tissue (skin), muscle, bone, and organ tissue. A solid tissue refers to any biological tissue in a subject that is not a body fluid. In the case of solid tissue, the tissue may be mechanically disrupted for an efficient extraction of the pyridine nucleotide. Tissue disruption techniques which do not destroy pyridine nucleotides are preferred. Such techniques include, for example, osmotic disruption, cell wall digestion, chemical cell membrane lysis, hand homogenizer, mincing, grinding, blade homogenizer (blender type, and tissue homogenizer), grinding with abrasives, French press, ultrasonication, bead mill and Manton-Gaulin homogenizers, are known. Tissue disruption methods are known and disclosed in standard biochemical texts such as Scopes (Protein Purification, Springer Verlag, New York, N.Y. 1988; incorporated herein by reference). Among the tissue disruption techniques, the technique of freezing the tissue followed by manual grinding (mortar and pestle) and the technique of using a tissue homogenizer are especially preferred.

Preferably, the tissue to be used is freshly collected from a subject. However, some sample tissues such as blood may be kept at room temperature for up to four days before the assay. Blood samples may be kept longer, such as up to about one week at about 4° C., up to about one month at about −20° C., or up to about two years or more at cryogenic temperatures of about −70° C. (dry ice, freezer, liquid nitrogen). Blood and tissue samples may be frozen directly. The stability of blood at room temperature is another advantage of the assay. Anticogulated blood may be sent from the collection site through express mail or regular mail for assays at a separate location without the need for refrigeration or other special handling.

The tissue is disrupted with simultaneous treatment in a basic solution. Tissue samples such as blood may be treated by basic solutions immediately. Before basic solution treatment, solid tissue may be preferably first disrupted using a technique that would not destroy the pyridine nucleotides. In a preferred embodiment, the compound used in the treatment with basic solution is sodium hydroxide (NaOH). In a preferred embodiment, basic treatment is performed at 4° C. for less than 2 minutes.

An additional step in the extraction is the reduction or removal of proteins in the sample. A reduction of the protein will eliminate or reduce undesirable reactions in the assay that may alter the results. Protein reduction or removal may be performed using any known protein removal steps such as, for example, salt precipitation, and acid precipitation. In a preferred embodiment, the protein is acid precipitated. Acid precipitation may comprise, for example, adding an equal volume of ice-cold 1 M $HClO_4$ to a solution, mixing, and chilling the solution on ice for ten minutes. The sample is then centrifuged to pellet the precipitated protein on the bottom of a centrifuge tube. In a preferred embodiment, the sample may be centrifuged at about 850 g's for about 10 minutes in a chilled centrifuge. However, any other technique that can separate the precipitate from the solution is also contemplated. Other techniques include careful pipetting of the solution out of the tube, different centrifuge conditions, the removal of precipitate by filter, and other techniques known to separate a precipitate from solution. After protein precipitation, the supernatant, is neutralized with a neutralization solution such as KOH and saved for the assay.

The pyridine nucleotide may be reduced to a reduced pyridine nucleotide by the addition of a number of enzyme/enzyme substrate pairs. For example, if the pyridine nucleotide to be measured is NAD, the enzyme/enzyme substrate pair can be alcohol dehydrogenase and ethanol. If the pyridine nucleotide to be measured is NADP, the enzyme/enzyme substrate pair can be isocitrate dehydrogenase and isocitrate.

Other enzyme, enzyme substrate pairs are well known to those of skill in the art and may be found by consultation with standard biochemistry references. Examples of suitable NAD dependent (i.e., NAD specific) enzymes and substrate pairs include alcohol dehydrogenase and ethanol; malate dehydrogenase and malate; lactate dehydrogenase and lactate; NAD specific isoctirate dehydrogenase (cytoplasmic) and isocitrate; and glyceraldehyde-3-phosphate dehydrogenase and glyceraldehyde-3-phosphate. Examples of suitable NADP dependent enzymes and enzyme substrate pairs include glucose-6-phosphate dehydrogenase and glucose-6-phosphate; 6-phosphogluconate dehydrogenase and 6-phosphogluconate; malic enzyme and malate; NADP specific isocitrate dehydrogenase (mitochondrial) and isocitrate.

NAD and NADP can be measured simultaneously by separating the reaction into two parts and adding an enzyme/enzyme substrate pair such as alcohol dehydrogenase and ethanol to one part to measure NAD and adding a second enzyme/enzyme substrate pair such as isocitrate dehydrogenase and isocitrate to the second part to measure NADP.

The amount of pyridine nucleotide in a biological sample may be determined by a change in optical density of a dye. Suitable dyes include any dye that shows a change in optical density (i.e., changes color) upon absorption of an electron. An electron is transferred from the reduced NAD or reduced NADP to the electron acceptor dye molecule. In a preferred embodiment, the electron is first transferred to an electron transmitter compound, such as, for example, oxidized phenazine ethosulfate (PES(ox)). Other electron transmitter compounds are known. Examples of electron transmitter compounds include, for example, 5-methylphenazinium methylsulfate, 1-methoxy-5-methylphenazinium methylsulfate, and diaphorase (dihydrolipoamide reductase, EC 1.6.4.3). After electron transfer to the electron transmitter compound, the electron is transferred from the electron transmitter compound to the electron acceptor dye molecule. The electron acceptor dye molecule may be, for example, thiazolyl blue (MTT) or a tetrazolium salt dye such as 3,3'-(3,3'-dimethoxy-4,4'-biphenylene)-bis(2-(p-nitrophenyl)-2H-tetrazolium chloride)(=NBT); 3-(p-indophenyl)-2-(p-nitrophenyl)-5-phenyl-2H-tetrazolium chloride(=INT); 3,3'-(4,4'-biphenylene)-bis(2,5-diphenyl-2H-tetrazoliumchloride); 3,3'-(3,3'-dimethoxy-4,4'- biphenylene)-bis(2,5-diphenyl-2H-tetrazolium chloride); and 3,3'-(3,3'-bis(2,5-bis(p-nitrophenyl)-2H-tetrazolium chloride).

The amount of optical density change in the electron acceptor dye molecule is related to the amount of NAD or NADP in the sample. An optical density change refers to an increase or decrease of absorbance (absorption) at a specific wavelength. In the context of this invention, when the electron acceptor dye used displays a change in absorbance characteristic at the visible wavelength, a change in color may be visible. The amount of change in absorbance may be correlated to the amount of pyridine nucleotide in the sample. This correlation may be performed roughly by using a judgement by eye and more accurately by a photospectrometer. The method of the invention is also adaptable to the use of an electron acceptor dye compound that exhibits an absorbance change in the infrared and ultraviolet region. While such dyes would not have a visible absorbance change, the change can be measured using a photospectrometer.

It is understood that when this invention refers to the optical density of a chemical, such as an electron acceptor dye, it is referring to the degree of opacity of a translucent solution of the chemical expressed by log (Io/I) where "Io" refers to the intensity of the incident ray and "I" is the intensity of the transmitted ray. Optical density may be expressed as a percent transmission or an absorbance at a certain wavelength. The values for absorbance (optical density) and transmission (or percent transmission) are interconvertable according to known formulas. The optical density of a solution can be measured using commercially available photospectrometry equipment (Beckman, Fullerton, Calif.). It is understood that when the electron acceptor dye is incorporated into a solid substance, such as a dipstick, the optical density of the dye may be estimated by the color of the dye substrate.

The amount of optical density change is correlated to the amount of pyridine nucleotide present in the biological sample. To ascertain the amount of pyridine nucleotide present, a standard curve of optical density values for the acceptor dye may be made. For example, a standard curve may be made by performing the method of the invention using a pyridine concentration of 0.01 pg/ml, 0.03 pg/ml, 0.06 pg/ml, 0.1 pg/ml, 0.3 pg/ml, 0.6 pg/ml, 1 pg/ml, 3 pg/ml, 6 pg/ml, 10 pg/ml, 30 pg/ml, 60 pg/ml, 100 pg/ml, 300 pg/ml, 600 pg/ml, and 1 ng Depending on the reaction volume and conditions, the optical density of the electron acceptor dye will generally have a sigmoidal curve. The characteristic of a sigmoidal curve is that at concentrations below the effective range of the assay, the amount of absorbance change is small to insignificant with respect to a change in pyridine nucleotide concentration. At the effective range, there is a repeatable absorbance change that is roughly proportional to the amount of pyridine nucleotides present. At the saturated range, where there is too much pyridine nucleotide for the assay, the amount of optical density change is once again small to insignificant with respect to a change in pyridine nucleotide concentration. In a preferred embodiment, the pyridine nucleotide measurement is made in the effective range of the assay. It should be noted that the effective range of the assay is where the amount of optical density change is repeatable with respect to the amount of pyridine nucleotide present. The relationship between the optical density change and amount of pyridine nucleotide at the effective range needs to be repeatable and reliable but it does not necessarily have to be linear. In a more preferred embodiment, the pyridine nucleotide measurement is made in the linear range of the assay.

After establishing a standard curve using known amounts of pyridine nucleotides (such as NAD or NADP), the concentration of a sample with unknown amounts of pyridine nucleotide may be calculated from standard colorimetric methods. Colorimetric methods for quantitating proteins (Bradford, Anal Biolchem 72, 248 (1976), J. Biol Chem 193, 265 (1951)), and pH, and which relies on absorbance measurements are known. One preferred method of determining the pyridine nucleotide concentration is to use standard curve fitting techniques to extrapolate the pyridine nucleotide concentration. For example, if one nanogram of pyridine nucleotide provides an absorbance reading of 0.5 and two nanograms of pyridine nucleotide provides an absorbance reading of 0.7, then an unknown sample with an absorbance reading of 0.6 may have about 1.5 nanograms. A second colorimetric method is to repeat the assay using different known amounts of pyridine nucleotides (NAD or NADP) until the optical density of the electron acceptor dye molecule is close to that of the unknown sample. Then the known amount of pyridine nucleotide used should reflect the pyridine nucleotide of the unknown sample. Both methods are accurate and contemplated by this invention.

The kits of the invention may be constructed in many physical forms. In its most preferred form, which is highly sensitive, the kit may include the following components. (1) a basic compound for the basic treatment of cells; (2) an acidic compound for the acid precipitation of proteins; (3) a neutralizing compound such as a buffer, a base, or an acid to restore a neutral pH to the reaction; (4) an enzyme/enzyme substrate pair to reduce the pyridine nucleotide; (5) and electron transfer compound; and (6) an electron acceptor dye. The kit may also include additional components such as anticoagulants for the collected blood, and instructions for performing the method of the invention. It is understood that the compounds of the kits may be in liquid solutions or in solid form. Liquid solutions may be preferred for ease in handling and for situations where only a few assays are to be performed per kit. In one embodiment, the kits of the invention may be packaged in single use containers that has sufficient reagents for one assay. Kits comprising compounds in solid forms may be preferred where it is desirable to mix chemical solutions together for multiple assays. Kits comprising solid components are also preferable where stability, reduced shipping costs and reduced handling costs are desired.

In addition, the kits of the invention may be optionally designed for electronic and mechanical means of measuring pyridine nucleotide content or concentration. For example, the dye may be supplied in disposable (e.g., plastic) cuvettes suitable for analysis by photospectrometry. Alternatively, the dye may be supplied in microtiter plates ready for analysis by a plate scanner (plate scanning photospectrometer).

The pyridine nucleotide measuring methods may also be used to assay a wide variety of pyridine nucleotide containing products of biological, agricultural and industrial origin. For example, the method and kits of the invention may be used to monitor the chemical manufacturer of $NAD^+$, NADPH, $NADP^+$ and NADPH. Therefore, the spirit and scope of the claims should not be limited to the description of the preferred versions contained herein.

Although the present invention has been described with reference to certain examples for purposes of clarification and illustration, it should be appreciated that certain obvious improvements and modifications can be practiced within the scope of the invention. For example, the biochemical reactions needed to perform the assay is independent of volume.

For purposes of illustration, an assay using 10 µL of starting material is disclosed. Obviously, if sample volume is limited, less starting material may be used and the reaction volume may be reduced. For example, a starting material of about 5 µL, about 3 µL, about 2 µL and even about 1 µL or less may be used. A number of problems, such as evaporation, may interfere with the assay in small volume reactions. However, techniques to overcome small volume assays are known. For example, the reaction may be performed in solution under oil or in a capillary to prevent evaporation. Optical density may be measured with instruments designed for small volumes (such as a laser photospectrometer). These techniques are known in the art and are also contemplated by the invention.

Alternatively, if the reaction is to be performed in the field where precision equipment or trained personnel is not available, a larger reaction volume may be used for easier manipulation. An increased reaction volume may comprise about 25 µL, about 50 µL, about 100 µL, about 250 µL, about 500 µL, about 750 µL, about 1 mL or more, and any volume in between.

It should be appreciated that the assay of the invention may be practiced using automated means such as a reaction/pipetting robot or machine. These robots and machines are commercially available and offer advantages of repeatability, consistency, and large throughput. Automatic systems, with automated liquid handling, linear robotic movement, robotic arms, scheduling and controlling software, and automated blood processing and analysis equipment are available from commercial suppliers such as Beckman (Fullerton, Calif.). Thus, a semiautomated or fully automated machine for the performance of the methods of the invention is also contemplated. Photospectrometers for analyzing individual wells of a microtiter dish for optical density (absorbance) is known.

It should be appreciated that while the assay of the invention is described as individual reactions, multiple assays may be performed in parallel in microtiter dishes and the like in a manual semiautomated or automated manner. Multiple parallel assays using microtiter dishes and multi-port pipets are known to those of skill in the art. The calculation of niacin numbers, NAD content, and NADP content may be performed automatically by computer means. Further, it is known that the accuracy of the assay may be improved by performing multiple assays on the same sample and averaging the results of the multiple assays to derive a more accurate reading.

Other embodiments and advantages of the invention are set forth, in part, in the description that follows and, in part, will be obvious from this description and may be learned from practice of the invention.

EXAMPLES

Example 1

Venipuncture Methods, Collection, and Storage of Blood Samples

Whole blood is collected in tubes containing either heparin or EDTA as anticoagulants. Because a sample of only about 10 µL to about 100 µL is needed for analysis, this sample may be derived from residual samples of blood drawn for other clinical analyses. If blood is to be drawn exclusively for assessment of niacin status, pediatric vacutainers may be used. Samples to be shipped or stored are conveniently frozen as 0.1 mL aliquots (suitable for about 10 assays at 10 µL per assay) in cryopreservation vials (Sigma, St Louis) stored at −80° C. or shipped on dry ice. NAD and NADP contents are stable in blood stored frozen for long periods of time (years) or for about one week at 4° C. or for up to about 4 days at room temperature (E. L. Jacobson et al., in ADP-Ribosylation Reactions, G. G. Poirier and P. Moreau, eds., p. 153. Springer-Verlag, New York, 1992.).

Example 2

Extraction of Total NAD and NADP from Blood

The extraction procedure of the present invention utilizes abase treatment step, followed by a neutralization step and a subsequent acid treatment step. In a preferred embodiment, one hundred microliters of whole blood is added to 1.0 mL of ice-cold 1 M NaOH. The sample is solubilized by vortexing and then adjusted to pH 7.0 by the addition of 0.25 mL of a 2.0 M $H_3PO_4$ neutralization solution. The sample is preferably kept below 4° C. and the total time in alkali is preferably less than 2.0 min to avoid loss of oxidized nucleotides. When extracting frozen samples, the NaOH is added to the frozen aliquot of blood, which is dislodged mechanically and solubilized by vortexing. Thawing prior to addition of the NaOH is to be avoided because it will result in loss of pyridine nucleotides. Protein is removed from the sample by precipitation with an equal volume (1.1 mL) of ice-cold 1 M $HClO_4$. After 10 min at 4° C., the sample is centrifuged at 850 g for 10 min. Two milliliters of the supernatant is removed to a new tube and adjusted to pH 7.0 to 7.3 by addition of 1.0 mL of 1 M KOH. At this point the sample may be stored frozen or held for 10 min at 4° C. and centrifuged at 850 g to remove the $HClO_4$ precipitate and then frozen. If the precipitate is removed prior to freezing, it is important to watch for and remove any additional salt that might form during the freezing process. This procedure extracts total $NAD^-$, NADH, $NADP^+$, and NADPH, because exposure of the blood cell preparation to acid results in complete oxidation of the reduced nucleotides due to the presence of hemoglobin. Further, the extracts are stable at −20° C. for more than two years and do not contain either inhibitors or substances that yield false-positive responses in the NAD or NADP assays. Finally, this procedure employing both alkaline and acid extraction effectively removes NAD(P) glycohydrolase activity.

Example 3

Computer-Linked Microplate Assays

In brief, a sample containing pyridine nucleotides to be assayed is contacted with a solution containing an enzyme/substrate pair, an electron acceptor molecule and an electron accepting dye molecule. The enzyme substrate pair causes any oxidized pyridine nucleotides present in the sample to become reduced. The reduced pyridine nucleotides react with the electron acceptor molecule causing the pyridine nucleotide to become oxidized with the concomitant reduction of an intermediate electron transfer compound. The intermediate electron transfer compound then reacts with the electron accepting dye molecule causing the oxidation of the electron acceptor and the reduction of the dye molecule. Upon reduction, the dye molecule undergoes a measurable change in optical density. The resulting cycling of NAD and intermediate electron acceptor results in signal amplification as the amount of dye molecule reduced far exceeds but is directly proportional to the amount of NAD in the assay. Thus, the presence of pyridine nucleotides in the sample solution results in a measurable change in the optical density of a dye molecule.

With reference to FIG. 1, a sample containing NAD is mixed with alcohol dehydrogenase (ADH) in the presence of ethanol. The NAD⁻present in the sample is reduced to NADH. The reduced NADH reacts in solution with oxidized phenazine ethosulfate (PES(ox)) resulting in the oxidation of the NADH to NAD with the concomitant production of the reduced form of PES(red). The reduced form of PES reacts with the oxidized form of thiazolyl blue (MTT) producing reduced MTT. The reduced form of MTT can be quantified by the optical m density at either 570 or 600 nm. When assaying NADP, the combination of isocitrate and m NADP-specific isocitrate dehydrogenase is substituted for ethanol and ethanol dehydrogenase.

Those skilled in the art will recognize that other enzyme substrate pairs may be used in place of those exemplified. Any enzyme/substrate pair that results in the specific reduction of NAD and NADP, respectively may be used to practice the invention. Selection of such enzyme/substrate pairs is routine to those skilled in the art. Also, other electron acceptors and dye molecules, including fluorescent dye molecules, may be used to practice the present invention. Any electron acceptor that reacts with pyridine nucleotides and is capable of transferring electrons to a dye molecule may be used in placed of the electron acceptor molecule exemplified above. Likewise any dye molecules that can accept electrons and undergo a measurable change in absorbance (optical density) characteristics may be used.

These assays have been adapted for microplates (microtiter plates), each well of which accommodates a volume of about 300 $\mu$L. Both NAD and NADP assays are conducted in the absence of direct light at 30° C. Absorbance can be measured in a microplate reader at either 570 or 600 nm. Sensitivity can be controlled by the length of the assay, as this is a kinetic assay in which NAD or NADP is the rate-limiting component that determines the amount of oxidation of the dye, thiazolyl blue (MTT). Because it is not necessary to terminate the assay to read the absorbance in a microplate reader, incubation can be extended and repeated measurements made to achieve the desired range of sensitivity.

TABLE II

MICROPLATE ASSAY COMPOSITION

| Component | Volume ($\mu$L) |
|---|---|
| Standard or sample | 100 |
| Diluent or H$_2$O | 100 |
| Mix | 100 |

For convenience each assay is composed of three components, each totaling 100 $\mu$L as shown in Table II. Diluent is a salt solution containing the exact composition of the final medium resulting from extraction of cells or tissues. Mix contains the buffers, salts, dyes, protein, and dehydrogenase. A premix solution containing all of the components of the mix except phenazine ethosulfate and enzyme, which are not stable frozen with the other components, at can be prepared in advance and stored frozen at −20° C. in convenient-sized aliquots. Just prior to initiation of the assay, phenazine ethosulfate and enzyme are added to the premix to form the complete mix. Addition of the mix to the wells initiates the reaction. A standard curve on each microplate is recommended. In all cases, three replicates are used for both standards and samples. The percent standard deviation of the mean rarely exceeds 5%. The amount of NAD and NADP determined is directly proportional to the amount of extract assayed. The NAD and NADP in the extracts are stable over at least a 90 minute assay period. Potential inhibitors or enhancers of the assay can be identified in extracts by comparing the response of a standard added to an assay well containing extract, relative to the response of the extract alone. Potentially interfering substances in the extracts that contribute to absorbance, which is not due to NAD or NADP, can be identified and quantified by conducting the assays in the absence of enzyme. The data can be corrected by subtracting these values from those obtained in the presence of the enzyme.

NAD Assay Components:

Standard: For the standard curve, varying amounts of NAD+ standard dissolved in H$_2$O are placed in the wells of the microplate and sufficient H$_2$O is added to make up 100 $\mu$L. A standard curve ranging from 0 to 100 pmol allows a wide range of sensitivity. The NAD+ standard is stored frozen at approximately 10 mM and is diluted to 1000 pmol/mL as determined spectrophotometrically by enzymatic conversion to NADH. The $A_{340}$ formed from NAD$^+$ on the addition of alcohol dehydrogenase (0.66 mg/mL; Sigma, St. Louis, Mo.) in 65 mM glycine (pH 8.8), and 0.1 M ethanol determines the exact concentration of NAD$^+$, using $6.22 \times 10^3$ liters·mol$^{-1}$·cm$^{-1}$ as extinction coefficient. The buffer containing Na$_2$P$_2$O$_7$, semicarbazide hydrochloride and glycine can be stored stably at 4° C. for a maximum of 5 months.

Samples: If it is desirable to assay less than 100 $\mu$L of sample, this difference in volume is adjusted using diluent.

Diluent: In the wells containing unknown samples 100 $\mu$L of H$_2$O is added, whereas in the wells containing standards 100 $\mu$L of diluent is added.

NAD mix: Mix is made just before addition to the assay by combining 5 volume of NAD premix with 1 volume of alcohol dehydrogenase (Sigma), 1 mg/mL in 0.1 M Bicine, pH 8.0 (stored frozen), and 1 volume of 40 mM phenazine ethosulfate (Sigma), which is stored in a light-proof container at 4° C. Mix should not be exposed to direct light. NAD premix is conveniently prepared in 100-mL lots as described in Table III and stored frozen in 15-mL light-proof tubes.

TABLE III

NAD PREMIX

| Stock solution | Volume (mL) | Storage conditions | In premix | Final concentration In assay |
|---|---|---|---|---|
| Ethanol, 10 M | 24 | Refrigerator | 2.4 M | 570 mM |
| Bicine, 1.5 M, pH 7.8 | 32 | Refrigerator | 0.48 M | 114 mM |
| MTT,[a] 10 mM | 20 | Freezer, dark | 2.0 mM | 0.48 mM |
| EDTA,[b] 0.2 M | 10 | Freezer | 20 mM | 4.8 mM |
| Bovine serum albumin, 100 mg/mL | 4 | Freezer | 4 mg/mL | 1 mg/mL |
| H$_2$O | 10 | | | |

[a]MTT, Thiazolyl blue.
[b]EDTA, Ethylenediaminetetraacetic acid.

NADP Assay Components:

Standard curve and samples: Prepare as previously described for the NAD assay. The NADP⁻ standard is stored frozen at approximately 10 mM and is diluted to 1000 pmol/mL as determined spectrophotometrically by enzymatic conversion to NADPH. The $A_{340}$ formed from NADP$^-$ on the addition of NADP-specific isocitrate dehydrogenase (0.1 mg/mL; Sigma) in 0.05 M isocitrate, 43 mM Bicine, pH 8.0, determines the exact NADP$^+$ concentration, using $6.22\times10^3$ liters·mol$^-$$_1$·cm$^{-1}$ as the extinction coefficient.

NADP mix: Make just before addition to the assay by combining 5 volume of NADP premix with 0.28 volume of 40 mM phenazine ethosulfate, and 0.72 mL of H$_2$O. The NADP mix should not be exposed to direct light. NADP premix is prepared and stored similarly to the NAD premix described above, as detailed in Table IV.

TABLE IV

NADP PREMIX

| Stock solution | Volume (mL) | Storage conditions | In premix | Final concentration In assay |
|---|---|---|---|---|
| Isocitrate, 0.2 M | 15 | Refrigerator (4° C.) | 30 mM | 7.1 mM |
| Phosphate buffer, 1.0 M, pH 6.8 | 32 | Refrigerator (4° C.) | 320 mM | 76 mM |
| MTT,[a] 10 mM | 20 | Freezer (−20° C.), dark | 2 mM | 0.48 mM |
| MgCl$_2$, 0.2 M | 15 | Refrigerator (4° C.) | 30 mM | 7 mM |
| Bovine serum albumin, 100 mg/mL | 4 | Freezer (−20° C.) | 4 mg/mL | 1 mg/mL |
| H$_2$O | 14 | | | |

[a]MTT, Thiazolyl blue.

If the microplate reader is linked to a computer equipped with software for analysis of spectrophotometric assays, computation of NAD and NADP in the assay and per milliliter of blood, and niacin number (NAD/NADP×100), can be computer generated and stored in a spreadsheet that can be downloaded to databases used in large studies. These assays are low in cost, amenable to automation, and thus are suitable for research or large-scale screening of niacin status in the human population.

Example 4

Methods for the Study of Niacin Status in Nonhematologic Tissues

Red blood cell NAD content is a reporter of human niacin status (C. S. Fu et al., *J. Nutr.* 119, 1949 (1989)). To date, little is known regarding the distribution of different forms of niacin to other human tissues or their efficiency of conversion to NAD. This represents a major gap in understanding human niacin metabolism. Yet proliferating cells are sensitive to NAD depletion during limited niacin nutriture (E. L. Jacobson et al., in ADP-Ribosylation Reactions, G. G. Poirier and P. Moreau, eds., p. 153. Springer-Verlag, New York, 1992; E. L. Jacobson et al., *J. Cell. Physiol.* 99, 417 (1979)). Thus, tissues or cells that undergo frequent turnover, including breast, skin, and the lining of the gastrointestinal tract, are likely targets for suboptimal niacin nutriture. Similar to the findings in erythrocytes, several tissues demonstrate changes in NAD content during modulation of niacin nutriture, while the NADP pool remains relatively constant (E. L. Jacobson et al., in ADP-Ribosylation Reactions, G. G. Poirier and P. Moreau, eds., p. 153. Springer-Verlag, New York, 1992; E. L. Jacobson et al., *J. Cell. Physiol.* 99, 417 (1979), E. L. Jacobson et al., *Cancer Res.* 37, A279 (1996)). This has led to development of the following methods for the study of the relationship of niacin status in blood to other tissues.

Extraction of NAD and NADP from Solid Tissues

Tissues obtained surgically are quick-frozen in liquid nitrogen and stored at −80° C. A mortar and pestle set is used to grind tissues to a fine powder in liquid nitrogen. The powder is transferred with a chilled spatula to a 50 mL centrifuge tube containing 1.0 mL of ice-cold 1.0 M NaOH. The sample is vortexed until dissolved and neutralized to pH 7.0 with 0.25 mL of 2.0 M H$_3$PO$_4$. The total length of time in alkali prior to neutralization should be less than 2 min to avoid loss of oxidized nucleotides. If the weight of tissue is to be obtained, the tube containing the NaOH is re-weighed and weighed again after neutralization. The suggested extraction volumes apply to tissue samples weighing 50 to 300 mg and may be scaled accordingly.

At this point the reduced nucleotides are converted to the oxidized forms by addition of 0.125 mL of 2.0 mM phenazine ethosulfate. Protein is removed from the sample by precipitation using an equal volume (1.4 mL) of ice-cold 1 M HClO$_4$. After 10 min on ice, the sample is centrifuged at 850 g for 10 min at 4° C. A known volume (2.4 mL) of the supernatant is removed to a new tube and adjusted to pH 7.0–7.3 by addition of 1.2 mL of 1 M KOH. The sample may be stored frozen; or it can be held at 4° C. to remove the KClO$_4$ precipitate, and then frozen. Protein or DNA quantifications may be performed on the HClO$_4$ precipitate as a reference for quantifying NAD and NADP in the tissues. If a tissue homogenizer is available (e.g., Polytron homogenizer; Brinkmann, Westbury, N.Y.) this extraction can be simplified. The frozen tissue is weighed and dropped into a Corex glass centrifuge tube containing the NaOH described above and homogenized immediately. The extract is neutralized immediately and processed as described above.

Example 5

Measurement of Redox State of NAD and NADP Pools

Much interest in understanding pyridine nucleotide metabolism has focused on the roles these nucleotides play in ADP-ribose transfer reactions. However, the availability of substrate for these reactions may depend on cellular redox state, particularly with regard to the formation of phosphocyclic ADP-ribose, because the NADP pool is maintained largely as NADPH. The following modifications to the above procedure have been developed to allow assessment of the redox state of these nucleotide pools.

The sample is placed in ice-cold 1.0 M NaOH extract and then divided into two equal aliquots. One aliquot is neutralized immediately with ice-cold H$_3$PO$_4$. This extract yields total pyridine nucleotides. The other aliquot is heated with stirring at 60° C. for 10 min neutralized, and chilled. The heating destroys oxidized nucleotides and the resulting extract is a measure of the reduced pyridine nucleotides. To obtain values for the oxidized nucleotides, the value obtained in the reduced sample is subtracted from the sample measuring total pyridine nucleotides. Any precipitate formed during neutralization is removed by centrifugation at 1500 g for 10 min at 4° C. These samples are assayed for NAD and NADP immediately, because the reduced pyridine nucleotides are not stable when frozen in aqueous solution. In this procedure, protein is not removed by an HClO$_4$ precipitation, thus residual NAD glycohydrolase activity may be present in some tissue extracts. This can be determined by checking the stability of the pyridine nucleotides in the extract as a function of time.

If tissues have or are suspected to have active NAD glycohydrolases, total pyridine nucleotides is obtained by employing the following modifications. The aliquot of NaOH extract that was immediately neutralized with $H_3PO_4$ is brought to 0.2 mM phenazine ethosulfate to oxidize the reduced pyridine nucleotides. The sample is then brought to 0.5 M $HClO_4$, set on ice for 15 min, and the precipitate is removed by centrifugation at 1500 g for 10 min at 4° C. The acid treatment step precipitates the glycohydrolase activity without affecting the oxidized nucleotides. The supernatant is transferred to another tube and neutralized with KOH and centrifuged to remove the $KClO_4$ precipitate, either before or after storage at −20° C.

Example 6

Results of Multiple Assays

Fresh or frozen blood samples were assayed using the procedure described in Example 3 with the following results. While the starting materials were the same, each assay was performed on a different day to test repeatability.

|  | NAD/ml | NADP/ml | NAD/NADP | Niacin Number |
|---|---|---|---|---|
| Fresh blood | 37021 | 22609 | 1.64 | 164 |
| Frozen blood | 30184 | 17182 | 1.66 | 166 |
| Frozen blood | 36280 | 19537 | 1.8 | 180 |
| Frozen blood | 30193 | 18900 | 1.6 | 160 |
| Frozen blood | 36720 | 20000 | 1.8 | 180 |
| Frozen blood | 31119 | 18871 | 1.65 | 165 |

Example 7

Kits for the Extraction and Analysis of Pyridine Nucleotides in Whole Blood Samples The present invention includes kits for the extraction of pyridine nucleotides from biological samples. The kits may contain some or all of the necessary reagents and solutions to practice the method described above. In a preferred embodiment, the kit will contain a base solution, a neutralizing solution and an acid solution. In a most preferred embodiment the base solution will be sodium hydroxide (NaOH), the neutralizing solution will be phosphoric acid ($H_3PO_4$), the acid solution will be perchloric acid ($HClO_4$) and KOH is supplied to neutralize perchloric acid.

The kits of the present invention may contain the reagents necessary to conduct the cycling assay used to determine the presence of pyridine nucleotides. For example, the kits of the present invention may contain enzyme/substrate pairs, electron acceptors and electron accepting dye molecules. The reagents may be in any form known to those skilled in the art. For example, the reagents may be supplied in solution or may be supplied as lyophilized powders. The reagents may be provided in bulk for dispensing by the user. In other embodiments, the reagents may be packaged in individual aliquots suitable for a single use.

The kit may further comprise instructions for performing the methods of the invention. The instructions may include, for example, detailed protocols for performing the assay described in claims and in the Example section of this application.

Although the present invention has been described with reference to certain examples for purposes of clarification and illustration, it should be appreciated that certain obvious improvements and modifications can be practiced within the scope of the appended claims and their equivalents. Other embodiments and uses of the invention will be apparent to those skilled in the art from consideration of the specification and practice of the invention disclosed herein. All supplies, including chemicals and laboratory ware, unless specifically noted, may be purchased from commercial sources such as Sigma (St. Louis). All patents and other references noted herein for whatever reason are specifically incorporated by reference. The specification and examples should be considered exemplary only with the true scope and spirit of the invention indicated by the following claims.

We claim:

1. A method to measure intracellular niacin status in a solid tissue sample comprising:

a) collecting a solid tissue sample;

b) extracting intracellular pyridine nucleotide from the solid tissue sample;

c) subjecting said pyridine nucleotide in the sample to a cycling process comprising one or more cycles of:
   reducing the pyridine nucleotide to a reduced pyridine nucleotide;
   transferring an electron from the reduced pyridine nucleotide to an electron acceptor dye molecule to produce a change in an absorbance of the electron acceptor dye molecule;

d) measuring the change in absorbance of the electron acceptor dye molecule to determine the intracellular niacin status for said solid tissue.

2. The method of claim 1 wherein the intracellular pyridine nucleotide is NAD or NADP.

3. The method of claim 1 wherein said extracting comprises:

a) disrupting cells of said solid tissue sample;

b) removing proteins therefrom.

4. The method of claim 3 wherein said disrupting comprises treating the whole blood cells with a basic compound and neutralizing the basic compound.

5. The method of claim 3 wherein said disrupting comprises:

disrupting the cells by mechanical means;

treating the cells with a basic compound; and neutralizing the basic compound.

6. The method of claim 3 wherein said removing comprises:

a) acid precipitation of proteins; and b) neutralization of the acid.

7. The method of claim 1 wherein the reducing step comprises adding an enzyme and enzyme substrate pair to the whole blood cells to reduce the pyridine nucleotide.

8. The method of claim 7 wherein the pyridine nucleotide is NAD, and the enzyme and enzyme substrate pair is a NAD specific enzyme and enzyme substrate pair.

9. The method of claim 8 wherein said NAD specific enzyme and enzyme substrate pair is selected from the group consisting of:

alcohol dehydrogenase and ethanol;

malate dehydrogenase and malate;

lactate dehydrogenase and lactate;

NAD specific isocitrate dehydrogenase and isocitrate;

glyceraldehyde-3-phosphate dehydrogenase and glyceraldehyde-3-phosphate;

and a combination thereof.

10. The method of claim 8 wherein the pyridine nucleotide is NADP, and the enzyme and enzyme substrate pair is a NADP specific enzyme and enzyme substrate pair.

11. The method of claim 10, wherein said NADP specific enzyme and enzyme substrate pair is selected from the group consisting of:

glucose-6-phosphate dehydrogenase and glucose-6 phosphate;

6-phosphogluconate dehydrogenase and 6-phosphogluconate;

malate dehydrogenase and malate;

NADP specific isocitrate dehydrogenase and isocitrate;

and a combination thereof.

12. The method of claim 1 wherein the transferring step further comprises:

a) transferring an electron from the reduced pyridine nucleotide to an electron transmitter compound;

b) transferring an electron from the electron transmitter compound to the electron acceptor dye molecule.

13. The method of claim 12 wherein said electron transmitter compound is selected from the group consisting of oxidized phenazine ethosulfate (PES(ox)); 5-methylphenazinium methylsulfate; 1-methoxy-5-methylphenazinium methylsulfate; diaphorase (dihydrolipoamide reductase, EC 1.6.4.3.); and a combination thereof.

14. The method of claim 1 wherein said electron acceptor dye is selected from the group consisting of thiazolyl blue (MTT); 3,3'-(3,3'-dimethoxy-4,4'-biphenylene)-bis(2-(p-nitrophenyl)-2H-tetrazolium chloride)(NBT); 3-(p-indophenyl)-2-(p-nitrophenyl)-5-phenyl-2H-tetrazolium chloride (INT); 3,3'-(4,4'-biphenylene)-bis(2,5-diphenyl-2H-tetrazoliumchloride); 3,3'-(3,3'-dimethoxy-4,4$^1$-biphenylene)-bis(2,5-diphenyl-2H-tetrazolium chloride); 3,3'-(3,3'-bis(2,5-bis(p-nitrophenyl)-2H-tetrazolium chloride); and a combination thereof.

15. The method of claim 1, wherein said solid tissue is organ tissue.

16. The method of claim 1, wherein said solid tissue is skin, muscle, or bone tissue.

17. A method for calculating niacin status in a solid tissue sample, comprising:

(a) determining NAD context and NADP content of said solid tissue sample using the method of claim 1; and (b) determining niacin status from a ratio of said NAD content and NADP content.

* * * * *